United States Patent [19]

Hunter, III et al.

[11] Patent Number: 4,583,972
[45] Date of Patent: Apr. 22, 1986

[54] WOUND EVACUATOR

[75] Inventors: Robert R. Hunter, III, Westboro, Mass.; Robert E. Weston, Exeter, N.H.

[73] Assignee: Complex, Inc., Hampton, N.H.

[21] Appl. No.: 611,603

[22] Filed: May 18, 1984

[51] Int. Cl.⁴ .............................................. A61M 37/00
[52] U.S. Cl. ...................................... 604/133; 604/75
[58] Field of Search ................ 604/75, 187, 212, 213, 604/216, 35, 119, 73, 131–134, 182; 128/DIG. 24

[56] References Cited

U.S. PATENT DOCUMENTS

| 3,742,952 | 7/1973 | Magers et al. | 604/133 |
| 4,161,179 | 7/1979 | Abramson | 604/134 |
| 4,187,847 | 2/1980 | Loeser | 604/134 |
| 4,429,693 | 2/1984 | Blake et al. | 604/119 |
| 4,493,701 | 1/1985 | Bootman et al. | 604/73 |

FOREIGN PATENT DOCUMENTS 1013635 12/1977 Canada .............................. 604/134

Primary Examiner—P. E. Konopka
Attorney, Agent, or Firm—Blodgett & Blodgett

[57] ABSTRACT

Device for producing suction in a wound consisting of two-hinged plates that spring-biased apart and contain between them a disposable bag for receiving fluid.

6 Claims, 8 Drawing Figures

WOUND EVACUATOR

BACKGROUND OF THE INVENTION

In medical practice, there are certain types of surgical operations where a considerable amount of fluid is generated in the wound. It is necessary to remove not only the liquid, but also other particles that may intrude into the wound. Such particles can hamper healing and can bring about infection. Also, if there is any infection in the wound, the removal of pus and other detritus is important to prevent the formation of more bacteria. Years ago, it was the practice to use a wick that extended through the incision and soaked up such fluids. The difficulty with a wick is that bacteria residing in the wick tended to multiply and to increase the possibility of further infection. Eventually, it became the practice to use evacuating equipment, such as a vacuum pump, to keep the wound free of fluids. These pumps are very expensive and intricate and, for the latter reason, it became common for the bacteria and other contamination to remain in the pump. Furthermore, in order to remove such contamination, it was necessary to autoclave and otherwise sterilize the pump and all the accessory equipment. This was a complicated operation and was not entirely satisfactory for a number of reasons. These and other difficulties experienced with the prior art devices have been obviated in a novel manner by the present invention.

It is, therefore, an outstanding object of the invention to provide a wound evacuator including a disposable container.

Another object of this invention is the provision of a device for removing fluid from a wound by a vacuum suction process in which the non-disposable elements are easily sterilized.

A further object of the present invention is the provision of a wound evacuator which is simple in construction, which is inexpensive to manufacture, and which is capable of a long life of useful service with a minimum of maintenance.

It is another object of the instant invention to provide a wound evacuator that includes a transparent bag having markings to indicate the volume of the contents.

A still further object of the invention is the provision of a vacuum-type wound evacuator in which reflux action is minimized.

It is a further object of the invention to provide a device for evacuating a surgical wound, which device includes no electrical motors or electrical connections.

It is a still further object of the present invention to provide a wound evacuator which can be operated and the fluid container removed without possibility of the hospital attendant coming in contact with the fluids.

With these and other objects in view, as will be apparent to those skilled in the art, the invention resides in the combination of parts set forth in the specification and covered by the claims appended hereto.

SUMMARY OF THE INVENTION

In general, the invention consists of a wound evacuator having two relatively thin plates joined by a hinge at one edge portion. A spring subjects the plates to movement about the hinge from a first position in which the plates lie closer together to a second position in which the plates are further separated. A bag made of flexible material lies between the plates and is subjected to expansion as the plates are moved during the said movement from the first position to the second position.

More specifically, the plates are generally rectangular and the hinge is located along one end edge. The bag is located in the portion adjacent the opposed end edge. The bag is provided with pockets located on opposite sides, which pockets slide snugly over the portions of the plates adjacent the said opposed end edges.

BRIEF DESCRIPTION OF THE DRAWINGS

The character of the invention, however, may be best understood by reference to one of its structural forms, as illustrated by the accompanying drawings, in which.

DESCRIPTION OF THE PREFERRED EMBODIMENT

Figure 1:
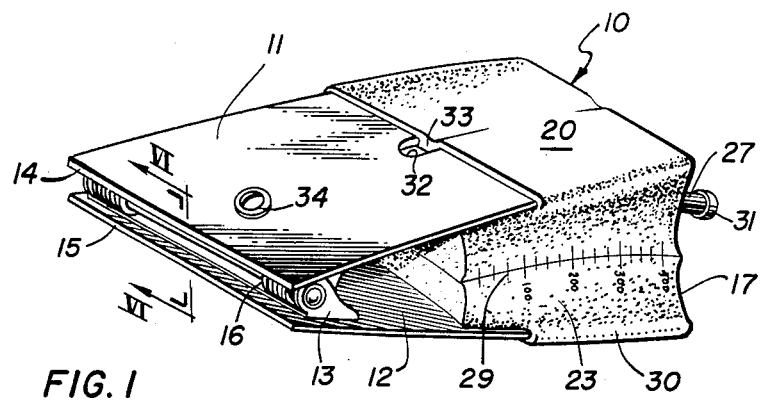
FIG. 1 is perspective view of a wound evacuator incorporating the principles of the present invention.

Referring first FIG. 1, wherein are best shown the general features of the invention, it can be seen that the wound evacuator, indicated generally by the reference numeral 10, is provided with two relatively thin plates 11 and 12. A hinge 13 joins the plates at the edge portions 14 and 15 and a spring 16 is provided to subject the plates to movement about the hinge from a first position (in which the plates lie closer together) to a second position in (which the plates are more separated). A bag 17 that is made of flexible material lies between the plates and is subjected to volume expansion as the plates are subjected to the said movement from the first position to the second position.

Figure 2:
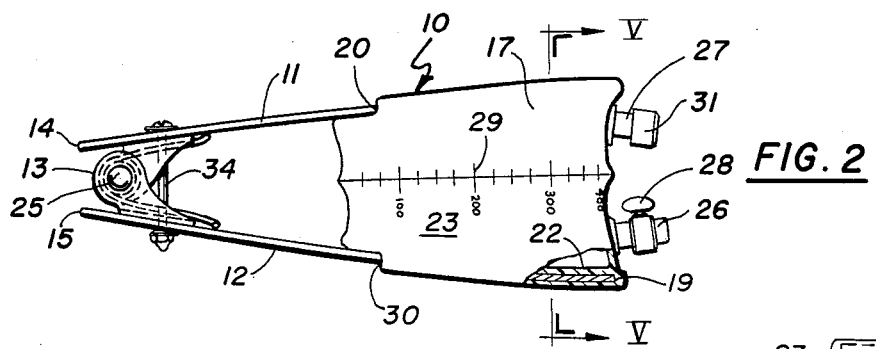
FIG. 2 is a side elevational view of the wound evacuator.
Figure 3:
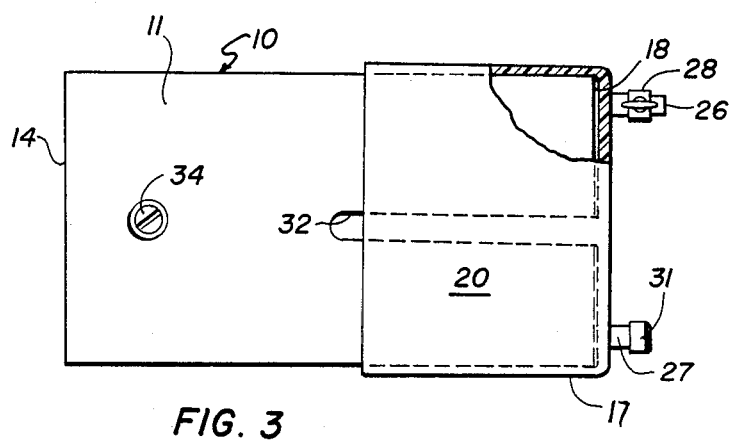
FIG. 3 is a top plan view of the wound evacuator.

As is evident in FIGS. 2 and 3, the plates 11 and 12 are generally rectangular and the hinge is located along first end edges 14 and 15, respectively. The bag 17 is located in the portion of the plates adjacent the opposed end edges 18 and 19, respectively.

Figure 8:
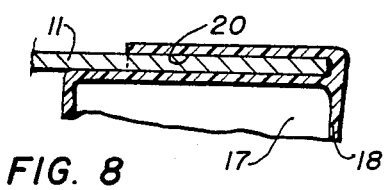
FIG. 8 is a vertical sectional view of the invention taken on the line VIII—VIII of FIG. 5.

The bag 17 is provided with pockets 20 and 30 located on opposite sides. These pockets slide snugly over the portions of the plates adjacent the said opposed end edges 18 and 19 (See FIG. 8).

Figure 5:
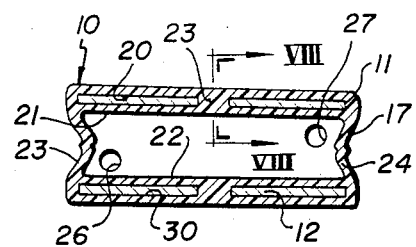
FIG. 5 is a sectional view of the invention taken on the line V—V of FIG. 2.

The bag 17 is in the general form of two opposed rectangular walls 21 and 22 (See FIG. 5) joined by two trapezoidal walls 23 and 24. This means that the bag is generally wedge-shaped to conform to the form of the space between the plates when the plates are in the second position.

Figure 6:
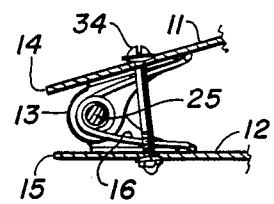
FIG. 6 is a vertical sectional view of the invention taken on the line VI—VI of FIG. 1.

As is evident in FIG. 6, the spring 16 is a torsion spring that is concentric with a hinge pin 25 lying between the plates 11 and 12 and extending parallel to and spaced from the inner surfaces of the plates. The hinge pin 25 is, of course, part of the hinge 13. A regulating bolt 34 extends through the plate 11 near the hinge pin 25 and is threaded into a suitable threaded insert in the plate 12 to limit the expansion of the plates and bag.

Figure 4:
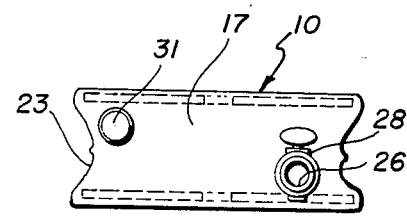
FIG. 4 is a front elevational view of the wound evacuator.

The bag 17 is formed of a sheet material that is impermeable to air and fluid and has access consisting only an inlet tube 26 and an outlet tube 27 whose locations are shown in FIG. 4. The inlet tube has an anti-reflex valve 28. The valve is of the check-valve type having a flapper or similar construction to allow only one way movement of fluid. In the preferred embodiment the bag is formed of polyvinyl/chloride sheet.

As is evident in FIGS. 1 and 2, the bag 17 is formed of translucent material and is provided with gradation markings to indicate the amount of the contents.

Figure 7:
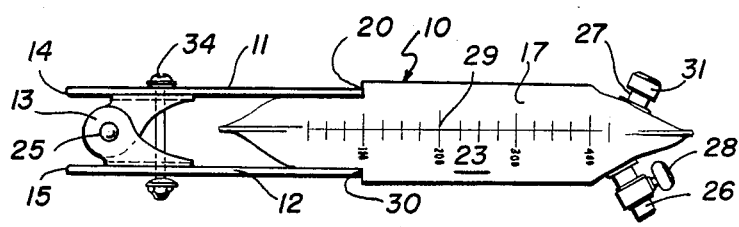
FIG. 7 is a side elevational view of the invention shown in a first condition.

The operation and advantages of the invention will now be readily understood in view of the above description. In order to use the wound evacuator, it is placed adjacent the patient and the plates 11 and 12 are then pressed together to force air out of the bag 17 through the exit tube 27. The inlet tube 26 is then attached to a tube which is passed to a tubing which lies within the wound. This tubing is of the conventional type having perforations for the admission of fluid but otherwise cutting off the end of the tube. The tubing is tightly sewn within the incision to render it more or less air tight. While these connections are being made, the plate 11 is pressed downwardly, causing the bag 17 to have the collapsed condition shown in FIG. 7. After all of the connections are made and a cap is placed on the exit tube 27, the plate 11 is released and the torsion spring 16 is allowed to bias the upper plate 11 upwardly and away from the bottom plate 12. This brings about a suction on the interior of the bag 17, because the outlet tube 27 has been cut off once the bag has been compressed. The suction that comes about serves to draw fluid from the wound into the bag, but there is no return of this fluid (even when large quantities are contained in the bag), because of the presence of the anti-reflux or check valve 28.

When the fluid fills the bag 17 to a suitable amount, the connection to the tube leading to the wound is disconnected and the bag can be grasped and pulled from the plates 11 and 12 by holding it vertically. The markings 29 will indicate the amount of fluid in the bag and this quantity can be recorded on the patient's chart. The container with its contents can then be disposed of in a suitable manner. One possibility is to drain the contents through the outlet tube 27 and then discard the bag; also, it may be desirable the bag and contents to throw the bag and contents away together.

In order to reintroduce the suction to the wound, it is only necessary to insert a new bag 17 on the plates 11 and 12 by inserting the end edges 18 and 19 of the plates 11 and 12, respectively, into the pockets 20 and 30 of the new bag 17. As is evident in FIG. 8, because the pockets 20 and 30 have recesses that terminate on a front wall and are pockets only, the ends of the plates 11 and 12 can be pushed down to the bottom of the pockets and thus locate the bag 17 in exactly the right position for maximum evacuation of the wound.

Because the bag is transparent, the contents can be observed at all times and the bag removed when it has reached a full condition. It can be noted that the outlet tube 27 is provided with a cap which can be removed during removal of air from the bag and then inserted, so that vacuum is formed within the bag. The plate 11 is provided with a longitudinal slot 32 in which is received a web 33 running down the center of the pocket 20. A similar slot and web is formed in the pocket 30 and the plate 11. These interconnections serve to prevent the centers of the bag from being drawn away from the plates.

The present apparatus is very simple in construction and, therefore, not be readily rendered inoperative even in the worst conditions. The fact that the bag is disposable assumes that the hospital attendants do not touch the fluid and, therefore, are not subjected to possible infection as might be experienced with other types of more complicated equipment. The disposability of the bag 17, which in affect is a combination pump and container, also assures that the bacteria and the like in one patient's wound fluids does not contaminate the apparatus when used with another patient. Furthermore, in testing the amount of fluid before disposal, one can be sure that it was not contaminated with fluid from another patient. The replacement of a used bag with a new bag is a relatively simple matter, since it simply involves inserting the free ends of the plates 11 and 12 into the pockets 20 and 30. Furthermore, since the bag 17 is made of an inexpensive plastic, it can be readily formed by ordinary plastic forming methods so as to be sold relatively cheaply.

It is obvious that minor changes may be made in the form and construction of the invention without departing from the material spirit thereof. It is not, however, desired to confine the invention to the exact form herein shown and described, but it is desired to include all such as properly come within the scope claimed.

The invention having been thus described, what is claimed as new and desired to secure by Letters Patent is:

1. Wound evacuator, comprising:
(a) two relatively thin plates of generally rectangular shape,
(b) a hinge joining the plates at one end edges,
(c) a spring located at the hinge for subjecting the plates to movement about the hinge from a first position in which the plates lie closer together to a second position in which the plates are more separated, and
(d) a bag made of flexible material lying between the plates in the portions adjacent the opposite free end edges and subjected to expansion as the plates are subjected to the said movement from the first position to the second position, the bag being provided with pockets located on opposite sides, which pockets slide snugly over the portions of the plates adjacent the said free end edges.

2. Wound evacuator as recited in claim 1, wherein the bag is in teh general form of two opposed rectangular walls joined by two trapezoidal walls, so as to be generally wedge-shaped to conform to the shape of the space between the plates when the plates are in the said second position.

3. Wound evacuator as recited in claim 1, wherein the spring is a torsion spring that is concentric with a hinge pin lying between the plates and extending parallel to and spaced from the inner surfaces of the plates.

4. Wound evacuator as recited in claim 1, wherein the bag is formed of impermeable sheet material and has access consisting only of an inlet tube and outlet tube, the inlet tube including an anti-reflux valve, while the outlet tube is provided with a removable closure.

5. Wound evacuator as recited in claim 4, wherein the bag is formed of polyvinyl chloride sheet.

6. Wound evacuator as recited in claim 1, wherein the bag is formed of transparent material and is provided with gradation markings to indicate the amount of the contents.

* * * * *